United States Patent
Kasemi et al.

(10) Patent No.: US 11,680,132 B2
(45) Date of Patent: Jun. 20, 2023

(54) HARDENER FOR EPOXY RESINS

(71) Applicant: SIKA TECHNOLOGY AG, Baar (CH)

(72) Inventors: Edis Kasemi, Zürich (CH); Andreas Kramer, Zürich (CH); Ursula Stadelmann, Zürich (CH); Urs Burckhardt, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 157 days.

(21) Appl. No.: 17/269,403

(22) PCT Filed: Oct. 1, 2019

(86) PCT No.: PCT/EP2019/076563
§ 371 (c)(1),
(2) Date: Feb. 18, 2021

(87) PCT Pub. No.: WO2020/070112
PCT Pub. Date: Apr. 9, 2020

(65) Prior Publication Data
US 2021/0246257 A1     Aug. 12, 2021

(30) Foreign Application Priority Data

Oct. 1, 2018   (EP) ..................................... 18197992

(51) Int. Cl.
*C08G 59/50*  (2006.01)
*C07C 211/27*  (2006.01)
*C09D 163/00*  (2006.01)
*C09J 163/00*  (2006.01)

(52) U.S. Cl.
CPC ........ *C08G 59/5033* (2013.01); *C07C 211/27* (2013.01); *C08G 59/5006* (2013.01); *C09D 163/00* (2013.01); *C09J 163/00* (2013.01)

(58) Field of Classification Search
CPC ............ C08G 59/5033; C08G 59/5006; C09D 163/00; C09J 163/00; C07C 211/27

USPC .......................................................... 156/300
See application file for complete search history.

(56) References Cited

U.S. PATENT DOCUMENTS 2,739,981 A * 3/1956 Szabo .................. C07D 499/00
562/595

FOREIGN PATENT DOCUMENTS

| DE | 28 53 752 | A1 | 10/1979 | |
| DE | 2853752 | A  * | 10/1979 | ............. C08G 59/50 |
| EP | 2 943 464 | B1 | 3/2017 | |
| EP | 3 138 863 | A1 | 3/2017 | |
| EP | 3 144 335 | A1 | 3/2017 | |
| EP | 3 375 802 | A1 | 9/2018 | |
| WO | 2016/023839 | A1 | 2/2016 | |

OTHER PUBLICATIONS

Lester Szabo et al., DE 2853752 A1 machine translation in English, Oct. 31, 1979 (Year: 1979).*
Nov. 18, 2019 Search Report issued in International Patent Application No. PCT/EP2019/076563.
Nov. 18, 2019 Written Opinion of the International Searching Authority issued in International Patent Application No. PCT/EP2019/076563.

* cited by examiner

*Primary Examiner* — David T Karst
(74) *Attorney, Agent, or Firm* — Oliff PLC

(57) ABSTRACT

A curing agent for epoxy resins has N-benzylethane-1,2-diamine and N,N'-dibenzylethane-1,2-diamine in a weight ratio in the range from 65/35 to 95/5. The curing agent is easy to prepare, thins epoxy resins particularly well, and enables low-emission epoxy resin products that have good workability and a long pot-life, cure reliably and surprisingly fast and can be walked on after a short time, in particular even in cold conditions. Coatings of particularly high mechanical grade, with a high surface quality and a minimal tendency to yellowing, can thus be produced. Epoxy resins of this type are particularly suitable for coating floors.

20 Claims, No Drawings

HARDENER FOR EPOXY RESINS

TECHNICAL FIELD

Curing agents for epoxy resins, epoxy resin compositions and the use thereof, especially as coating.

STATE OF THE ART

Epoxy resin-based coatings are widely used in the building trade. They consist of liquid resin and curing agent components, which are mixed before application and then cure at ambient temperatures in the range from about 5 to 35° C. to form a material of high strength and stability. Such epoxy resin coatings have a tendency to surface defects such as haze, spots, roughness or tack, which is also referred to as "blushing". Blushing is caused by the amines present in the curing agent component forming a salt with carbon dioxide ($CO_2$) from the air and occurs particularly at high humidity and low temperatures. Especially in esthetically demanding coating applications such as floor coatings, the occurrence of blushing-related surface defects is extremely disadvantageous and usually necessitates laborious reworking or overcoating of the faulty areas or often even of the entire coating.

The viscosity of an epoxy resin composition is reduced using thinners so that it is easy to apply and gives good wetting of the substrate surfaces. At the same time, thinners also reduce the susceptibility to blushing. The customary thinners, such as benzyl alcohol, are volatile compounds (VOC or SVOC) that are not incorporated into the polymer matrix during curing and thus may result in emissions. For low-emission products, for which there is a growing demand from consumers, this means that thinners may be used only in small amounts or not at all.

For reduction of blushing and as reactive diluent, it is possible to use alkylated amines in the curing agent component, as described in EP 2,943,464, WO 2016/023839, EP 3,138,863 or EP 3,144,335. N-Benzylethane-1,2-diamine, as described in EP 3,138,863, is particularly suitable. Epoxy resin coatings obtained therewith, however, are still in need of improvement.

SUMMARY OF THE INVENTION

It is an object of the present invention to provide a curing agent for epoxy resins which overcomes the disadvantages of the prior art and is especially suitable for esthetically demanding coating applications.

This object is achieved by the curing agent as described in claim 1, comprising a particular combination of N-benzylethane-1,2-diamine and N,N'-dibenzylethane-1,2-diamine. The curing agent of the invention has low viscosity and gives particularly good thinning of an epoxy resin composition, which means that it can be formulated in low-emission form and nevertheless has good processability as a coating. The curing agent of the invention additionally enables surprisingly rapid curing under moist and cold conditions, such as, in particular, 8° C./80% relative humidity. As a result, the coating can be walked upon even after a short time, typically within the first 24 hours after application, and can be processed further, for example recoated or sealed. And the curing agent of the invention ultimately achieves particularly good results in the surface quality of the cured coating. Compared to the use of N-benzylethane-1,2-diamine alone, the additional use of N,N'-dibenzylethane-1,2-diamine in the weight ratio claimed enables faster curing and high surface quality under moist and cold conditions, and better processability, without any distinct impairment in final hardness or curing under standard climatic conditions (23° C./50% relative humidity). This is particularly surprising, given that one would expect distinctly slowed curing and a lower final hardness owing to the lower functionality of N,N'-dibenzylethane-1,2-diamine.

The curing agent of the invention is easy to prepare, especially via the reductive alkylation of ethane-1,2-diamine with benzaldehyde and hydrogen. It gives particularly good thinning of epoxy resins and enables low-emission epoxy resin products having good processability and long pot life, which cure reliably and surprisingly rapidly and can soon be walked on, especially also under moist and cold conditions. This especially gives rise to mechanically high-quality coatings having high surface quality and a low tendency to yellowing. Such epoxy resin products are particularly suitable as a coating for floors.

Further aspects of the invention are the subject of further independent claims. Particularly preferred embodiments of the invention are the subject of the dependent claims.

Ways of Executing the Invention

The invention provides a curing agent for epoxy resins comprising N-benzylethane-1,2-diamine and N,N'-dibenzylethane-1,2-diamine in a weight ratio in a range from 65/35 to 95/5.

A "primary amino group" refers to an amino group which is bonded to a single organic radical and bears two hydrogen atoms; a "secondary amino group" refers to an amino group which is bonded to two organic radicals which may also together be part of a ring and bears one hydrogen atom; and a "tertiary amino group" refers to an amino group which is bonded to three organic radicals, two or three of which may also be part of one or more rings, and does not bear any hydrogen atom.

"Amine hydrogen" refers to the hydrogen atoms of primary and secondary amino groups.

"Amine hydrogen equivalent weight" refers to the mass of an amine or an amine-containing composition that contains one molar equivalent of amine hydrogen. Substance names beginning with "poly", such as polyamine or polyepoxide, refer to substances containing, in a formal sense, two or more of the functional groups that occur in their name per molecule.

A "thinner" refers to a substance that is soluble in an epoxy resin and lowers its viscosity, and that is not chemically incorporated into the epoxy resin polymer during the curing process.

"Molecular weight" refers to the molar mass (in g/mol) of a molecule. "Average molecular weight" refers to the number average $M_n$ of a polydisperse mixture of oligomeric or polymeric molecules, which is typically determined by means of gel permeation chromatography (GPC) against polystyrene as standard.

"Pot life" refers to the duration of processibility of an epoxy resin composition, i.e. the maximum possible time span between the mixing of the components and the application of the mixed composition in which it is in a sufficiently free-flowing state and is able to wet the substrate surfaces.

"Open time" of an adhesive refers to the maximum time span possible for a cohesive bond between the application of the adhesive and the joining of the parts to be bonded.

"Room temperature" refers to a temperature of 23° C.

The curing agent is preferably not water-based. It especially contains less than 10% by weight, preferably less than 5% by weight, more preferably less than 2.5% by weight, of water. Such a curing agent is particularly suitable for the curing of non-emulsified epoxy resins and enables very hydrophobic and stable materials.

The curing agent is preferably largely free of N,N-dibenzylethane-1,2-diamine, i.e. the diamine having one tertiary and one primary amino group. The curing agent preferably contains less than 2% by weight, more preferably less than 1% by weight, especially less than 0.5% by weight of N,N-dibenzylethane-1,2-diamine, based on the total amount of N-benzylethane-1,2-diamine and N,N'-dibenzylethane-1,2-diamine.

The weight ratio between N-benzylethane-1,2-diamine and N,N'-dibenzylethane-1,2-diamine is preferably in the range from 70/30 to 90/10, especially 80/20 to 90/10. Such a curing agent enables a particularly attractive combination of good thinning, rapid curing and high surface quality.

N-Benzylethane-1,2-diamine and N,N'-dibenzylethane-1,2-diamine are preferably prepared via the reductive alkylation of ethane-1,2-diamine with benzaldehyde and hydrogen.

The reductive alkylation is preferably conducted in the presence of a suitable catalyst. Preferred catalysts are palladium on charcoal (Pd/C), platinum on charcoal (Pt/C), Adams' catalyst or Raney nickel, especially palladium on charcoal or Raney nickel.

The reductive alkylation is preferably conducted in a pressure apparatus at a hydrogen pressure of 5 to 150 bar, especially 10 to 100 bar. This can be effected in a batchwise process or preferably in a continuous process.

The reductive alkylation is preferably conducted at a temperature in the range from 40 to 120° C., especially 60 to 100° C.

N-Benzylethane-1,2-diamine and N,N'-dibenzylethane-1,2-diamine may be prepared individually and blended in the weight ratio appropriate for the curing agent of the invention.

N-Benzylethane-1,2-diamine and N,N'-dibenzylethane-1,2-diamine are preferably prepared together, by conducting the reductive alkylation in a particular molar ratio between ethane-1,2-diamine and benzaldehyde, which leads to a reaction mixture comprising both amines.

The molar ratio between ethane-1,2-diamine and benzaldehyde is more preferably chosen such that the weight ratio between N-benzylethane-1,2-diamine and N,N'-dibenzylethane-1,2-diamine in the resultant reaction mixture corresponds to that of the curing agent of the invention.

The molar ratio of ethane-1,2-diamine to benzaldehyde is preferably in the range from 5/1 to 1.5/1, more preferably in the range from 4/1 to 2/1. Such a reaction mixture can be used to prepare the curing agent of the invention directly without any need to add separately prepared N-benzylethane-1,2-diamine or N,N'-dibenzylethane-1,2-diamine.

The curing agent of the invention thus preferably comprises a reaction mixture obtained from the reductive alkylation of ethane-1,2-diamine with benzaldehyde and hydrogen, comprising N-benzylethane-1,2-diamine and N,N'-dibenzylethane-1,2-diamine in a weight ratio in the range from 65/35 to 95/5, preferably 70/30 to 90/10, especially 80/20 to 90/10.

The curing agent of the invention preferably comprises at least one further amine.

Preferred further amines are aliphatic, cycloaliphatic or araliphatic polyamines having at least 2, especially at least 3, amine hydrogens, such as, in particular, 2,2-dimethylpropane-1,3-diamine, pentane-1,3-diamine (DAMP), pentane-1,5-diamine, 1,5-diamino-2-methylpentane (MPMD), 2-butyl-2-ethylpentane-1,5-diamine (C11 neodiamine), hexane-1,6-diamine, 2,5-dimethylhexane-1,6-diamine, 2,2 (4),4-trimethylhexane-1,6-diamine (TMD), heptane-1,7-diamine, octane-1,8-diamine, nonane-1,9-diamine, decane-1,10-diamine, undecane-1,11-diamine, dodecane-1,12-diamine, 1,2-, 1,3- or 1,4-diaminocyclohexane, 1,3-bis(aminomethyl)cyclohexane, 1,4-bis(aminomethyl)cyclohexane, bis(4-aminocyclohexyl)methane, bis(4-amino-3-methylcyclohexyl)methane, bis(4-amino-3-ethylcyclohexyl)methane, bis(4-amino-3,5-dimethylcyclohexyl)methane, bis(4-amino-3-ethyl-5-methylcyclohexyl)methane, 1-amino-3-aminomethyl-3,5,5-trimethylcyclohexane (isophoronediamine or IPDA), 2(4)-methyl-1,3-diaminocyclohexane, 2,5(2,6)-bis(aminomethyl)bicyclo[2.2.1]heptane (NBDA), 3(4),8(9)-bis(aminomethyl)tricyclo[5.2.1.0$^{2,6}$]decane, 1,4-diamino-2,2,6-trimethylcyclohexane (TMCDA), menthane-1,8-diamine, 3,9-bis(3-aminopropyl)-2,4,8,10-tetraoxaspiro[5.5]undecane, 1,3-bis(aminomethyl)benzene (MXDA), 1,4-bis(aminomethyl)benzene, bis(2-aminoethyl) ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine, 4,7,10-trioxatridecane-1,13-diamine or higher oligomers of these diamines, bis(3-aminopropyl)polytetrahydrofuran or other polytetrahydrofurandiamines, cycloaliphatic diamines containing ether groups from the propoxylation and subsequent amination of 1,4-dimethylolcyclohexane, especially obtainable as Jeffamine® RFD-270 (from Huntsman), or polyoxyalkylenedi- or -triamines, especially Jeffamine® D-230, Jeffamine® D-400, Jeffamine® D-2000, Jeffamine® EDR-104, Jeffamine® EDR-148, Jeffamine® EDR-176, Jeffamine® T-403, Jeffamine® T-3000, Jeffamine® T-5000 (all from Huntsman), or corresponding amines from BASF or Nitroil, 2-aminoethylpiperazine, 3-dimethylaminopropylamine (DMAPA), 3-(3-(dimethylamino)propylamino) propylamine (DMAPAPA), bis(6-aminohexyl)amine (BHMT), diethylenetriamine (DETA), triethylenetetramine (TETA), tetraethylene-pentamine (TEPA), pentaethylenehexamine (PEHA) or higher homologs of linear polyethyleneamines, dipropylenetriamine (DPTA), N-(2-aminoethyl) propane-1,3-diamine (N3 amine), N,N'-bis(3-aminopropyl) ethylenediamine (N4 amine), N,N'-bis(3-aminopropyl)-1,4-diaminobutane, N5-(3-aminopropyl)-2-methylpentane-1,5-diamine, N3-(3-aminopentyl)pentane-1,3-diamine, N5-(3-amino-1-ethylpropyl)-2-methylpentane-1,5-diamine, N,N'-bis(3-amino-1-ethylpropyl)-2-methylpentane-1,5-diamine, N-benzyldiethylenetriamine, N-benzyltriethylenetetramine, N,N'-dibenzyltriethylenetetramine, N'''-benzyl-N,N'-bis(3-aminopropyl)ethylenediamine, N''',N''''-dibenzyl-N,N'-bis(3-aminopropyl)ethylenediamine, N-benzylpropane-1,2-diamine, N,N'-dibenzylpropane-1,2-diamine, N-benzyl-1,3-bis(aminomethyl)benzene, N,N'-dibenzyl-1,3-bis(aminomethyl)benzene, N-(2-ethylhexyl)-1,3-bis(aminomethyl)benzene, N,N'-bis(2-ethylhexyl)-1,3-bis(aminomethyl)benzene, styrenized MXDA (available as Gaskamine® 240 from Mitsubishi Gas Chemical), adducts of the abovementioned or further polyamines with epoxides or epoxy resins, especially adducts with diepoxides or monoepoxides, or polyamidoamines, especially reaction products of a mono- or polybasic carboxylic acid or ester or anhydride thereof, especially a dimer fatty acid, with an aliphatic, cycloaliphatic or aromatic polyamine used in stoichiometric excess, especially a polyalkyleneamine, for example DETA or TETA, or Mannich bases, especially phenalkamines, i.e. reaction products of phenols, especially cardanol, with aldehydes, especially formaldehyde, and polyamines.

The curing agent preferably comprises at least one further amine selected from the group consisting of TMD, 1,2-, 1,3- or 1,4-diaminocyclohexane, 1,3-bis(aminomethyl)cyclohexane, 1,4-bis(aminomethyl)cyclohexane, bis(4-aminocyclohexyl)methane, IPDA, 2(4)-methyl-1,3-diaminocyclohexane, MXDA, polyoxypropylenediamines having an average molecular weight $M_n$ in the range from 200 to 500 g/mol, DMAPAPA, BHMT, DETA, TETA, TEPA, PEHA, DPTA, N3 amine, N4 amine, adducts of these or further polyamines with mono- or diepoxides and Mannich bases.

Among these, preference is given to TMD, 1,3-bis(aminomethyl)cyclohexane, IPDA, MXDA, DMAPAPA, BHMT, DETA, TETA, TEPA, PEHA, DPTA, N3 amine, N4 amine or adducts thereof with mono- or diepoxides, especially adducts thereof with bisphenol A or bisphenol F diglycidyl ether. The additional use of such an amine can enable a particularly high hardness or a particularly high glass transition temperature.

Among these, preference is further given to an adduct of MPMD or propane-1,2-diamine with cresyl glycidyl ether, especially ortho-cresyl glycidyl ether. The adduct formation is preferably performed with an excess of MPMD or propane-1,2-diamine over cresyl glycidyl ether, and the amine that has not formed an adduct is preferably removed after the reaction by means of distillation.

The curing agent may preferably comprise a combination of two or more of the further amines mentioned.

A particularly preferred further amine is IPDA. Such a curing agent is widely available and inexpensive, and enables epoxy resin products having particularly high hardness and glass transition temperature.

A particularly preferred further amine is also MXDA. Such a curing agent is widely available and inexpensive, and enables epoxy resin products having particularly rapid curing and high glass transition temperature.

A particularly preferred further amine is also TETA, TEPA, PEHA or N4 amine. Such a curing agent is widely available and particularly inexpensive, and enables epoxy resin products having particularly rapid curing, high hardness and high glass transition temperature.

A particularly preferred further amine is also DMAPAPA, especially for use in epoxy resin adhesives. This affords particularly high strengths and bonding forces.

The curing agent of the invention may preferably also comprise a combination of two or more such further amines.

Such further amines are preferably used in such an amount that 0.1 to 10, preferably 0.2 to 5, mol of amine hydrogens from further amines is present per mole of amine hydrogen from N-benzylethane-1,2-diamine and N,N'-dibenzylethane-1,2-diamine.

The curing agent optionally comprises at least one thinner.

Especially suitable are xylene, 2-methoxyethanol, dimethoxyethanol, 2-ethoxyethanol, 2-propoxyethanol, 2-isopropoxyethanol, 2-butoxyethanol, 2-phenoxyethanol, 2-benzyloxyethanol, benzyl alcohol, ethylene glycol, ethylene glycol dimethyl ether, ethylene glycol diethyl ether, ethylene glycol dibutyl ether, ethylene glycol diphenyl ether, diethylene glycol, diethylene glycol monomethyl ether, diethylene glycol monoethyl ether, diethylene glycol mono-n-butyl ether, diethylene glycol dimethyl ether, diethylene glycol diethyl ether, diethylene glycol di-n-butyl ether, propylene glycol butyl ether, propylene glycol phenyl ether, dipropylene glycol, dipropylene glycol monomethyl ether, dipropylene glycol dimethyl ether, dipropylene glycol di-n-butyl ether, diphenylmethane, diisopropylnaphthalene, mineral oil fractions, for example Solvesso® grades (from Exxon), alkylphenols such as tert-butylphenol, nonylphenol, dodecylphenol, cardanol (from cashewnutshell oil, containing 3-(8,11,14-pentadecatrienyl)phenol as its main constituent), styrenized phenol, bisphenols, aromatic hydrocarbon resins, especially types containing phenol groups, alkoxylated phenol, especially ethoxylated or propoxylated phenol, especially 2-phenoxyethanol, adipates, sebacates, phthalates, benzoates, organic phosphoric or sulfonic esters or sulfonamides.

Preferred thinners have a boiling point of more than 200° C.

The thinner is preferably selected from the group consisting of benzyl alcohol, styrenized phenol, ethoxylated phenol, aromatic hydrocarbon resins containing phenol groups, especially the Novares® LS 500, LX 200, LA 300 or LA 700 grades (from Rütgers), diisopropylnaphthalene and cardanol.

Particular preference is given to benzyl alcohol.

Thinners containing phenol groups are also effective as accelerator.

The curing agent optionally comprises at least one accelerator.

Suitable accelerators are substances which accelerate the reaction between amino groups and epoxy groups, especially acids or compounds hydrolyzable to acids, especially organic carboxylic acids such as acetic acid, benzoic acid, salicylic acid, 2-nitrobenzoic acid, lactic acid, organic sulfonic acids such as methanesulfonic acid, p-toluenesulfonic acid or 4-dodecylbenzenesulfonic acid, sulfonic esters, other organic or inorganic acids such as, in particular, phosphoric acid, or mixtures of the aforementioned acids and acid esters; nitrates such as calcium nitrate in particular; tertiary amines such as, in particular, 1,4-diazabicyclo[2.2.2]octane, benzyldimethylamine, α-methylbenzyldimethylamine, triethanolamine, dimethylaminopropylamine, imidazoles such as, in particular, N-methylimidazole, N-vinylimidazole or 1,2-dimethylimidazole, salts of such tertiary amines, quaternary ammonium salts, such as, in particular, benzyltrimethylammonium chloride, amidines such as, in particular, 1,8-diazabicyclo[5.4.0]undec-7-ene, guanidines such as, in particular, 1,1,3,3-tetramethylguanidine, phenols, especially bisphenols, phenolic resins or Mannich bases such as, in particular, 2-(dimethylaminomethyl)phenol, 2,4,6-tris(dimethylaminomethyl)phenol or polymers of phenol, formaldehyde and N,N-dimethylpropane-1,3-diamine, phosphites such as, in particular, di- or triphenyl phosphites, or compounds having mercapto groups.

Preferred accelerators are acids, nitrates, tertiary amines or Mannich bases. Particular preference is given to salicylic acid or calcium nitrate or 2,4,6-tris(dimethylaminomethyl) phenol or a combination thereof.

Most preferred is a combination of calcium nitrate and 2,4,6-tris(dimethylaminomethyl)phenol. This achieves particularly rapid curing, especially also at low temperatures, and particularly high hardnesses.

Calcium nitrate is especially used in the form of an aqueous solution having 20% to 70% by weight of calcium nitrate.

The present invention further provides an epoxy resin composition comprising
- a resin component comprising at least one epoxy resin and
- a curing agent component comprising the above-described curing agent containing N-benzylethane-1,2- diamine and N,N'-dibenzylethane-1,2-diamine in a weight ratio of 65/35 to 95/5, preferably 70/30 to 90/10, especially 80/20 to 90/10.

A suitable epoxy resin is obtained in a known manner, especially from the oxidation of olefins or from the reaction of epichlorohydrin with the polyols, polyphenols or amines.

Suitable epoxy resins are especially aromatic epoxy resins, especially the glycidyl ethers of:

bisphenol A, bisphenol F or bisphenol A/F, where A stands for acetone and F for formaldehyde, which served as reactants for the preparation of these bisphenols. In the case of bisphenol F, positional isomers may also be present, especially derived from 2,4'- or 2,2'-hydroxyphenylmethane.

dihydroxybenzene derivatives such as resorcinol, hydroquinone or catechol;

further bisphenols or polyphenols such as bis(4-hydroxy-3-methylphenyl)methane, 2,2-bis(4-hydroxy-3-methylphenyl)propane (bisphenol C), bis(3,5-dimethyl-4-hydroxyphenyl)methane, 2,2-bis(3,5-dimethyl-4-hydroxyphenyl)propane, 2,2-bis(3,5-dibromo-4-hydroxyphenyl)propane, 2,2-bis(4-hydroxy-3-tert-butylphenyl)propane, 2,2-bis(4-hydroxyphenyl)butane (bisphenol B), 3,3-bis(4-hydroxyphenyl)pentane, 3,4-bis(4-hydroxyphenyl)hexane, 4,4-bis(4-hydroxyphenyl)heptane, 2,4-bis(4-hydroxyphenyl)-2-methylbutane, 2,4-bis(3,5-dimethyl-4-hydroxyphenyl)-2-methylbutane, 1,1-bis(4-hydroxyphenyl)cyclohexane (bisphenol Z), 1,1-bis(4-hydroxyphenyl)-3,3,5-trimethylcyclohexane (bisphenol TMC), 1,1-bis(4-hydroxyphenyl)-1-phenylethane, 1,4-bis[2-(4-hydroxyphenyl)-2-propyl]benzene (bisphenol P), 1,3-bis[2-(4-hydroxyphenyl)-2-propyl]benzene (bisphenol M), 4,4'-dihydroxydiphenyl (DOD), 4,4'-dihydroxybenzophenone, bis(2-hydroxynaphth-1-yl)methane, bis(4-hydroxynaphth-1-yl)methane, 1,5-dihydroxynaphthalene, tris(4-hydroxyphenyl)methane, 1,1,2,2-tetrakis(4-hydroxyphenyl)ethane, bis(4-hydroxyphenyl) ether or bis(4-hydroxyphenyl) sulfone;

novolaks, which are especially condensation products of phenol or cresols with formaldehyde or paraformaldehyde or acetaldehyde or crotonaldehyde or isobutyraldehyde or 2-ethylhexanal or benzaldehyde or furfural;

aromatic amines such as aniline, toluidine, 4-aminophenol, 4,4'-methylenediphenyldiamine, 4,4'-methylenediphenyldi(N-methyl)amine, 4,4'-[1,4-phenylenebis(1-methylethylidene)]bisaniline (bisaniline P) or 4,4'-[1,3-phenylenebis(1-methylethylidene)]bisaniline (bisaniline M).

Further suitable epoxy resins are aliphatic or cycloaliphatic polyepoxides, especially glycidyl ethers of saturated or unsaturated, branched or unbranched, cyclic or open-chain di-, tri- or tetrafunctional $C_2$ to $C_{30}$ alcohols, especially ethylene glycol, propylene glycol, butylene glycol, hexanediol, octanediol, polypropylene glycols, dimethylolcyclohexane, neopentyl glycol, dibromoneopentyl glycol, castor oil, trimethylolpropane, trimethylolethane, pentaerythritol, sorbitol or glycerol, or alkoxylated glycerol or alkoxylated trimethylolpropane;

a hydrogenated bisphenol A, F or A/F liquid resin, or the glycidylation products of hydrogenated bisphenol A, F or A/F;

an N-glycidyl derivative of amides or heterocyclic nitrogen bases, such as triglycidyl cyanurate or triglycidyl isocyanurate, or reaction products of epichlorohydrin with hydantoin.

epoxy resins from the oxidation of olefins such as, in particular, vinylcyclohexene, dicyclopentadiene, cyclohexadiene, cyclododecadiene, cyclododecatriene, isoprene, 1,5-hexadiene, butadiene, polybutadiene or divinylbenzene.

The epoxy resin is preferably a liquid resin or a mixture containing two or more liquid epoxy resins.

"Liquid epoxy resin" refers to an industrial polyepoxide having a glass transition temperature below 25° C.

The resin component optionally additionally contains proportions of solid epoxy resin.

The epoxy resin is especially a liquid resin based on a bisphenol, in particular a bisphenol A diglycidyl ether and/or bisphenol F diglycidyl ether, as are commercially available, for example, from Olin, Huntsman or Momentive. These liquid resins have a low viscosity for epoxy resins and enable rapid curing and high hardnesses. They may contain proportions of solid bisphenol A resin or novolak glycidyl ethers.

The resin component may contain a reactive diluent.

Preferred reactive diluents are reactive diluents containing epoxy groups, especially butanediol diglycidyl ether, hexanediol diglycidyl ether, trimethylolpropane di- or triglycidyl ether, phenyl glycidyl ether, cresyl glycidyl ether, guaiacol glycidyl ether, 4-methoxyphenyl glycidyl ether, p-n-butylphenyl glycidyl ether, p-tert-butylphenyl glycidyl ether, 4-nonylphenyl glycidyl ether, 4-dodecylphenyl glycidyl ether, cardanol glycidyl ether, benzyl glycidyl ether, allyl glycidyl ether, butyl glycidyl ether, hexyl glycidyl ether, 2-ethylhexyl glycidyl ether, or glycidyl ethers of natural alcohols, such as, in particular, $C_8$- to $C_{10}$- or $C_{12}$- to $C_{14}$- or $C_{13}$- to $C_{15}$-alkyl glycidyl ethers.

The epoxy resin composition preferably contains at least one further constituent selected from the group consisting of thinners, accelerators and fillers.

Suitable accelerators are those already mentioned, especially salicylic acid, calcium nitrate or 2,4,6-tris(dimethylaminomethyl)phenol or a combination thereof. Most preferred is a combination of calcium nitrate and 2,4,6-tris(dimethylaminomethyl)phenol. This achieves particularly rapid curing, especially also at low temperatures, and particularly high hardnesses.

Suitable thinners are those already mentioned, especially those having a boiling point of more than 200° C.

The thinner is preferably selected from the group consisting of benzyl alcohol, styrenized phenol, ethoxylated phenol, aromatic hydrocarbon resins containing phenol groups, especially the Novares® LS 500, LX 200, LA 300 or LA 700 grades (from Rütgers), diisopropylnaphthalene and cardanol.

Particular preference is given to benzyl alcohol.

The epoxy resin composition preferably contains only a small content of thinners. It preferably contains less than 25% by weight, more preferably less than 15% by weight, especially less than 10% by weight, of thinners. This enables low-emission or emissions-free epoxy resin products.

Suitable fillers are, in particular, ground or precipitated calcium carbonate, which is optionally coated with fatty acid, in particular stearates, baryte (heavy spar), talc, quartz powder, quartz sand, silicon carbide, iron mica, dolomite, wollastonite, kaolin, mica (potassium aluminum silicate), molecular sieve, aluminum oxide, aluminum hydroxide, magnesium hydroxide, silica, cement, gypsum, fly ash, carbon black, graphite, metal powders such as aluminum, copper, iron, zinc, silver or steel, PVC powder or hollow beads.

Preference is given to calcium carbonate, quartz powder, and quartz sand.

The epoxy resin composition optionally comprises further auxiliaries and additives, in particular the following:

- reactive diluents, in particular those already mentioned above, or epoxidized soybean oil or linseed oil, compounds containing acetoacetate groups, in particular acetoacetylated polyols, butyrolactone, carbonates, aldehydes, isocyanates or silicones having reactive groups;
- solvents;
- further amines, especially monoamines such as, in particular, benzylamine or furfurylamine or aromatic polyamines such as, in particular, 4,4'-, 2,4' and/or 2,2'-diaminodiphenylmethane, 2,4- and/or 2,6-tolylenediamine, 3,5-dimethylthio-2,4-tolylenediamine and/or 3,5-dimethylthio-2,6-tolylenediamine, 3,5-diethyl-2,4-tolylenediamine and/or 3,5-diethyl-2,6-tolylenediamine;
- compounds having mercapto groups, in particular liquid mercaptan-terminated polysulfide polymers, mercaptan-terminated polyoxyalkylene ethers, mercaptan-terminated polyoxyalkylene derivatives, polyesters of thiocarboxylic acids, 2,4,6-trimercapto-1,3,5-triazine, triethylene glycol dimercaptan or ethanedithiol;
- polymers, in particular polyamides, polysulfides, polyvinyl formal (PVF), polyvinyl butyral (PVB), polyurethanes (PUR), polymers having carboxyl groups, polyamides, butadiene-acrylonitrile copolymers, styrene-acrylonitrile copolymers, butadiene-styrene copolymers, homo- or copolymers of unsaturated monomers, in particular from the group comprising ethylene, propylene, butylene, isobutylene, isoprene, vinyl acetate or alkyl (meth)acrylates, in particular chlorosulfonated polyethylenes or fluorine-containing polymers or sulfonamide-modified melamines;
- fibers, in particular glass fibers, carbon fibers, metal fibers, ceramic fibers or polymer fibers such as polyamide fibers or polyethylene fibers;
- pigments, in particular titanium dioxide, iron oxides or chromium(III) oxide;
- rheology modifiers, in particular thickeners or antisettling agents;
- adhesion improvers, in particular organoalkoxysilanes;
- flame-retardant substances, in particular the aluminum hydroxide or magnesium hydroxide fillers already mentioned, antimony trioxide, antimony pentoxide, boric acid $(B(OH)_3)$, zinc borate, zinc phosphate, melamine borate, melamine cyanurate, ammonium polyphosphate, melamine phosphate, melamine pyrophosphate, polybrominated diphenyl oxides or diphenyl ethers, phosphates such as, in particular, diphenyl cresyl phosphate, resorcinol bis(diphenylphosphate), resorcinol diphosphate oligomer, tetraphenylresorcinol diphosphite, ethylenediamine diphosphate, bisphenol A bis(diphenylphosphate), tris(chloroethyl) phosphate, tris(chloropropyl) phosphate, tris(dichloroisopropyl) phosphate, tris[3-bromo-2,2-bis(bromomethyl)propyl] phosphate, tetrabromobisphenol A, bis(2,3-dibromopropyl ether) of bisphenol A, brominated epoxy resins, ethylenebis(tetrabromophthalimide), ethylenebis(dibromonorbornanedicarboximide), 1,2-bis(tribromophenoxy)ethane, tris(2,3-dibromopropyl) isocyanurate, tribromophenol, hexabromocyclododecane, bis(hexachlorocyclopentadieno)cyclooctane or chloroparaffins; or
- additives, especially dispersed paraffin wax, film-forming auxiliaries, wetting agents, leveling agents, defoamers, deaerators, stabilizers against oxidation, heat, light or UV radiation, or biocides.

The epoxy resin composition preferably comprises further auxiliaries and additives, especially pigments, wetting agents, leveling agents and/or defoamers.

In the epoxy resin composition, the ratio of the number of groups reactive toward epoxy groups relative to the number of epoxy groups is preferably in the range from 0.5 to 1.5, in particular 0.7 to 1.2.

The primary and secondary amino groups present in the epoxy resin composition, and any other groups present that are reactive toward epoxy groups, react with the epoxy groups, resulting in ring opening (addition reaction) thereof. As a result primarily of this reaction, the composition polymerizes and thereby cures.

The resin component and the curing agent component of the epoxy resin composition are stored in separate containers. Further constituents of the epoxy resin composition may be present as a constituent of the resin component or of the curing agent component; further constituents reactive toward epoxy groups are preferably a constituent of the curing agent component. It is likewise possible for further constituents to be present as a dedicated, further component.

A suitable container for storage of the resin component or the curing agent component is especially a vat, a hobbock, a bag, a bucket, a can, a cartridge or a tube. The components are storable, meaning that they can be stored prior to use for several months up to one year or longer without any change in their respective properties to a degree relevant to their use. For the use of the epoxy resin composition, the components are mixed with one another shortly before or during application. The mixing ratio between the resin component and the curing agent component is preferably chosen such that the groups of the curing agent component that are reactive toward epoxy groups are in a suitable ratio to the epoxy groups of the resin component, as described above. In parts by weight, the mixing ratio between the resin component and the curing agent component is typically in the range from 1:10 to 10:1.

The components are mixed by means of a suitable method; this mixing may be done continuously or batchwise. If the mixing does not immediately precede the application, it has to be ensured that not too much time passes between the mixing of the components and the application and that the application is effected within the pot life. The mixing is especially effected at ambient temperature, which is typically within the range from about 5 to 40° C., preferably about 10 to 35° C. Curing by chemical reaction begins with the mixing of the two components, as described above. The curing typically proceeds at a temperature in the range from 0 to 150° C. It preferably proceeds at ambient temperature and typically extends over a few days to weeks. The duration depends upon factors including the temperature, the reactivity of the constituents, and the stoichiometry thereof, and on the presence of accelerators.

The epoxy resin composition is applied to at least one substrate, the following substrates being particularly suitable:

- glass, glass ceramic, concrete, mortar, cement screed, fiber cement, brick, tile, gypsum or natural rocks such as granite or marble;
- repair or leveling compounds based on PCC (polymer-modified cement mortar) or ECC (epoxy resin-modified cement mortar);

metals or alloys such as aluminum, iron, steel, copper, other nonferrous metals, including surface-upgraded metals or alloys such as galvanized or chrome-plated metals;

asphalt or bitumen;

leather, textiles, paper, wood, woodbase materials bonded with resins, e.g. phenolic, melamine or epoxy resins, resin-textile composites or further so-called polymer composites;

plastics, such as rigid and flexible PVC, polycarbonate, polystyrene, polyester, polyamide, PMMA, ABS, SAN, epoxy resins, phenolic resins, PUR, POM, TPO, PE, PP, EPM or EPDM, in each case untreated or surface-treated, for example by means of plasma, corona or flames;

fiber-reinforced plastics, such as carbon fiber-reinforced plastics (CFRP), glass fiber-reinforced plastics (GFRP) and sheet molding compounds (SMC);

insulation foams, especially made of EPS, XPS, PUR, PIR, rock wool, glass wool or foamed glass;

coated or painted substrates, especially painted tiles, coated concrete, powder-coated metals or alloys or painted metal sheets;

coatings, paints or varnishes, especially coated floors that are overcoated with a further floor covering layer.

If required, the substrates can be pretreated prior to application, especially by physical and/or chemical cleaning methods or the application of an activator or a primer.

The curing of the epoxy resin composition described affords a cured composition. The epoxy resin composition described is preferably used as coating, primer, adhesive, sealant, encapsulating compound, casting resin, or as matrix for fiber composites such as, in particular, CFRP or GFRP. The term "coating" also covers primers, paints, varnishes and sealants.

The epoxy resin composition described is more preferably used as a coating. Coatings are understood here to mean coverings of all kinds that are applied over an area, especially floor coverings, paints, varnishes, sealants, primers or protective coatings, especially also those for heavy-duty corrosion protection. The epoxy resin composition is particularly suitable as a floor covering or floor coating for interiors such as offices, industrial halls, gym halls or cooling spaces, or outdoors for balconies, terraces, parking decks, bridges or roofs, as a protective coating for concrete, cement, metals, plastics or wood, for example for surface sealing of wood constructions, vehicles, loading areas, tanks, silos, shafts, pipelines, machines or steel constructions, for example of ships, piers, offshore platforms, lock gates, hydroelectric power plants, river constructions, swimming pools, wind turbines, bridges, chimneys, cranes or sheet-pile walls, or as an undercoat, tiecoat or anticorrosion primer or for hydrophobization of surfaces.

Particularly advantageously, the epoxy resin composition described is used in low-emission coatings with environmental quality seals, for example according to Emicode (EC1 Plus), AgBB, DIBt, Der Blaue Engel, AFSSET, RTS (M1) and US Green Building Council (LEED).

For use as a coating, the epoxy resin composition advantageously has a fluid consistency with low viscosity and good leveling properties. The mixed composition is, within the pot life, typically applied to the surface of a substrate as a thin film having a layer thickness of about 50 µm to about 5 mm, typically at ambient temperature. Application is effected especially by pouring onto the substrate to be coated and subsequent homogeneous distribution with the aid, for example, of a coating bar or a notched trowel. Application can also be effected with a brush or roller or in the form of a spray application, for example as an anticorrosion coating on steel. Curing typically gives rise to substantially homogeneous, glossy and nontacky films of high hardness which have good adhesion to a wide variety of different substrates.

The invention further provides a method of coating, comprising the steps of (i) mixing the components of the epoxy resin composition described, (ii) applying the mixed composition to a substrate within the pot life, followed by the curing of the mixed composition.

It is possible to apply a further coating to the fully or partly cured composition, in which case said further layer may likewise be an epoxy resin composition, or else another material, especially a polyurethane or polyurea coating.

Particular preference is also given to using the epoxy resin composition described as an adhesive. When used as adhesive, after the components have been mixed, the epoxy resin composition typically has a pasty consistency with structurally viscous properties. On application, the mixed adhesive is applied within the pot life to at least one of the substrates to be bonded and the two substrates are joined to form an adhesive bond within the open time of the adhesive.

The mixed adhesive is applied especially by means of a brush, roll, spatula, doctor blade or trowel, or from a tube, cartridge or metering device.

The adhesive is particularly suitable for uses in the construction industry, especially for the reinforcement of built structures by means of steel lamellas or lamellas made of carbon fiber-reinforced composite plastics (CFRP), for constructions containing bonded precast concrete components, especially bridges or concrete towers, for example for wind turbines, shafts, pipelines or tunnels, or for constructions containing bonded natural rocks, ceramic elements or parts made of fiber cement, steel, cast iron, aluminum, wood or polyester, for the anchoring of anchors or steel bars in boreholes, for the fixing of, for example, handrails, railings or doorframes, for repairs such as, in particular, the filling of edges, holes or joins in concrete maintenance, or for the bonding of films of polyvinyl chloride (PVC), flexibilized polyolefin (Combiflex®) or adhesion-modified chlorosulfonated polyethylene (Hypalon®) to concrete or steel.

Further fields of use relate to structural bonding in the construction or manufacturing industry, especially as adhesive mortar, assembly adhesive, reinforcement adhesive such as, in particular, for the bonding of lamellas of CFRP or steel to concrete, brickwork or wood, as element adhesive, for example for bridge elements, sandwich element adhesive, facade element adhesive, reinforcing adhesive, bodywork adhesive or half-shell adhesive for rotor blades of wind turbines.

Such an epoxy resin adhesive is likewise suitable for the filling of cavities such as fissures, cracks or drillholes, wherein the adhesive is filled or injected into the cavity and fills it after curing, and bonds or sticks the flanks of the cavity to one another in a force-fitting manner.

The invention further provides a method of bonding, comprising the steps of (i) mixing the components of the epoxy resin composition described, (ii) applying the mixed composition within the pot life,
either to at least one of the substrates to be bonded and joining the substrates to form a bond within the open time, or into a cavity or gap between two or more substrates and optionally inserting an anchor into the cavity or gap within the open time, followed by the curing of the mixed composition.

An "anchor" refers here more particularly to a rebar, a threaded rod or a bolt. An anchor is especially adhesive-bonded or anchored in a wall, ceiling or foundation in such a way that a portion thereof is bonded in a force-fitting manner and a portion thereof protrudes and can be subjected to a construction load.

Identical or different substrates may be bonded.

The application and curing of the epoxy resin composition described, or the method of coating or the method of bonding, affords an article coated or bonded with the composition. This article may be a built structure or part thereof, especially a built structure above or below the ground, an office, an industrial hall, a sports hall, a chill room, a silo, a bridge, a roof, a staircase, a balcony, a terrace or a parking deck, or it may be an industrial good or a consumer good, especially a pier, an offshore platform, a lock gate, a crane, a bulkhead, a pipeline or a rotor blade of a wind turbine, or a mode of transport such as, in particular, an automobile, a truck, a rail vehicle, a ship, an aircraft or helicopter, or an installable component thereof.

The invention thus further provides an article obtained from the use described or the described method of coating or from the described method of bonding.

The epoxy resin composition described features advantageous properties. It also has low viscosity and good processibility with little or absolutely no thinner, has a long pot life, cures reliably and rapidly, and can soon be walked on, especially also under moist and cold conditions. This especially gives rise to coatings of high mechanical quality that have high surface quality and a low tendency to yellowing. Epoxy resin products of this kind are particularly suitable as coatings, especially for floors.

EXAMPLES

Working examples are adduced hereinafter, which are intended to elucidate the invention described. The invention is of course not limited to these described working examples.

"AHEW" stands for amine hydrogen equivalent weight.

"EEW" stands for epoxy equivalent weight.

"Standard climatic conditions" refer to a temperature of 23±1° C. and a relative air humidity of 50±5%.

Description of the Measurement Methods:

Viscosity was measured on a thermostated Rheotec RC30 cone-plate viscometer (cone diameter 50 mm, cone angle 1°, cone tip-plate distance 0.05 mm, shear rate 10 s$^{-1}$).

Amine value was determined by means of titration (with 0.1 N HClO$_4$ in acetic acid versus crystal violet).

Substances and Abbreviations Used

| | |
|---|---|
| Sikafloor ®-264N (A) | Sikafloor ®-264N component A (RAL 5005), filled pigmented resin component of an epoxy resin floor coating, EEW 450 g/eq (from Sika) |
| B-EDA | N-benzylethane-1,2-diamine, prepared as described below, AHEW 50 g/eq |
| DB-EDA | N,N'-Dibenzylethane-1,2-diamine, prepared as described below, AHEW 120 g/eq |
| B-EDA-mix | Reaction mixture comprising N-benzyl-ethane-1,2-diamine and N,N'-dibenzyl-ethane-1,2-diamine in a weight ratio of 85/15, prepared as described below, AHEW 55 g/eq |
| TEPA | tetraethylenepentamine, AHEW 30 g/eq (technical grade, from Huntsman) |
| IPDA | 3-aminomethyl-3,5,5-trimethylcyclohexylamine, AHEW 42.6 g/eq (Vestamin ® IPD, from Evonik) |
| Adduct-1 | adduct of propylene-1,2-diamine and technical grade o-cresyl glycidyl ether, prepared as described below, AHEW 90 g/eq |
| Ca nitrate solution | 50% by weight of calcium nitrate tetrahydrate in water |
| Ancamine ® K54 | 2,4,6-tris(dimethylaminomethyl)phenol (from Air Products) |

Reaction Mixture Comprising N-Benzylethane-1,2-diamine (B-EDA Mix)

A round-bottom flask was initially charged with 180.3 g (3 mol) of ethylene-1,2-diamine under a nitrogen atmosphere at room temperature. With good stirring, a solution of 106.0 g (1 mol) of benzaldehyde in 1200 ml of isopropanol was slowly added dropwise, and the mixture was stirred for 2 hours. The reaction mixture was then hydrogenated in a continuous hydrogenation apparatus with a Pd/C fixed bed catalyst at a hydrogen pressure of 80 bar, a temperature of 80° C. and a flow rate of 5 ml/min. To monitor the reaction, IR spectroscopy was used to check whether the imine band at about 1665 cm$^{-1}$ had disappeared. Thereafter, the hydrogenated solution was concentrated on a rotary evaporator at 65° C., removing unreacted ethylene-1,2-diamine, water and isopropanol. The reaction mixture thus obtained was a clear, pale yellowish liquid having an amine value of 678 mg KOH/g and a content, determined by means of GC, of N-benzylethane-1,2-diamine of about 81% by weight (retention time 8.47-8.57 min) and N,N'-dibenzylethane-1,2-diamine of about 14% by weight (retention time 14.27 min). This corresponds to a weight ratio between N-benzylethane-1,2-diamine and N,N'-dibenzylethane-1,2-diamine of 85/15.

N-Benzylethane-1,2-diamine (B-EDA)

50 g of the reaction mixture comprising N-benzylethane-1,2-diamine (B-EDA-mix), prepared as described above, was distilled at 80° C. under reduced pressure, with collection of 31.3 g of distillate at a vapor temperature of 60 to 65° C. and 0.06 mbar. What was obtained was a colorless liquid having a viscosity of 8 mPa·s at 20° C., an amine value of 750 mg KOH/g and a purity, determined by GC, of >97% (retention time 8.47-8.57 min).

N,N'-Dibenzylethane-1,2-diamine (DB-EDA)

A round-bottom flask was initially charged with 30.1 g (0.5 mol) of ethylene-1,2-diamine under a nitrogen atmosphere at room temperature. With good stirring, a solution of 111.5 g (1.1 mol) of benzaldehyde in 1000 ml of isopropanol was slowly added dropwise, and the mixture was stirred for 2 hours. The reaction mixture was then hydrogenated in a continuous hydrogenation apparatus with a Pd/C fixed bed catalyst at a hydrogen pressure of 80 bar, a temperature of 80° C. and a flow rate of 5 ml/min. To monitor the reaction, IR spectroscopy was used to check whether the imine band at about 1665 cm$^{-1}$ had disappeared. Thereafter, the hydrogenated solution was concentrated on a rotary evaporator at 65° C., removing unreacted benzaldehyde, water and isopropanol. The reaction mixture thus obtained was a clear, pale yellowish liquid. 100 g of this reaction mixture was distilled at 165° C. under reduced pressure, with collection of 90 g of distillate at a vapor temperature of 135° C. and 0.03 mbar. What was obtained was a colorless liquid having a viscosity of 31 mPa·s at 20° C., an amine value of 460 mg KOH/g and a purity, determined by means of GC, of 96% (retention time 14.27 min).

Adduct-1:

An initial charge of 4.15 kg of propylene-1,2-diamine under a nitrogen atmosphere was heated to 70° C. and then, with good stirring, 2.93 kg of Araldite® DY-K (o-cresyl glycidyl ether, technical grade, from Huntsman) was added gradually, with the temperature of the reaction mixture being from 70 to 80° C. After 1 hour at 80° C., the reaction mixture was cooled down and the volatile constituents were removed by distillation by means of a thin-film evaporator (0.5-1 mbar, jacket temperature 115° C.).

Production of Epoxy Resin Compositions:

EXAMPLES 1 TO 6

For each example, the ingredients of the curing agent component indicated in table 1 were mixed in the indicated amounts (in parts by weight) by means of a centrifugal mixer (SpeedMixer™ DAC 150, FlackTek Inc.) and stored with the exclusion of moisture.

The resin component used was Sikafloor®-264N comp. A (blue) (from Sika) in the amount specified in table 1 (in parts by weight).

The two components of each composition were then processed by means of the centrifugal mixer to give a homogeneous liquid and this was tested immediately as follows:

10 minutes after mixing, the viscosity was measured at 20° C. ("Viscosity (10')"). For the determination of Shore D hardness to DIN 53505, two cylindrical test specimens (diameter 20 mm, thickness 5 mm) in each case were produced. One was stored under standard climatic conditions and hardness was measured after 1 day and after 2 days (1 d SCC and 2 d SCC); the other was stored at 8° C. and 80% relative humidity and hardness was measured after 1 day and after 2 days in the cold state (1 d 8°/80% and 2 d 8°/80%).

A first film was applied to a glass plate in a layer thickness of 500 μm, and this was stored/cured under standard climatic conditions. König hardness (König pendulum hardness, measured according to DIN EN ISO 1522) was determined on this film after 1 day ("König hardness (1 d SCC)"), after 2 days ("König hardness (2 d SCC)"), after 4 days ("König hardness (4 d SCC)"), after 7 days ("König hardness (7 d SCC)") and after 14 days ("König hardness (14 d SCC)"). After 14 days, the appearance of the film was assessed (designated "Appearance (SCC)" in the table). A film was described as "nice" if it had a glossy and nontacky surface with no structure. "Structure" refers to any kind of marking or pattern on the surface. A film with a nontacky surface without structure and with reduced gloss was described as "matt".

A second film was applied to a glass plate in a layer thickness of 500 μm and immediately after application this was stored/cured for 7 days at 8° C. and 80% relative humidity and then for 2 weeks under standard climatic conditions. 24 hours after application, a polypropylene bottletop beneath which a damp sponge had been positioned was placed onto the film. After a further 24 hours, the sponge and the bottletop were removed and positioned at a new point on the film, from which it was in turn removed and repositioned after 24 hours, and this was done a total of 4 times. The appearance of this film was then assessed (designated "Appearance (8°/80%)" in the tables) in the same way as described for Appearance (SCC). Also reported in each case here was the number and kind of visible marks that had formed in the film as a result of the damp sponge and/or the bottletop on top. The number of white-colored spots was reported as "blushing". The intensity of any ring-shaped impression formed by sinking of the first bottletop applied 24 h after application was reported as "ring". Such a ring-shaped impression indicates that the coating is not ready to be walked upon. The König hardness was again determined on the films thus cured, in each case after 7 days at 8° C. and 80% relative humidity ("König hardness (7 d 8°/80%)") and then after a further 2 days under SCC ("König hardness (+2 d SCC)"), 7 days under SCC ("König hardness (+7 d SCC)"), and 14 d under SCC ("König hardness (+14 d SCC)").

As a measure of yellowing, the change in color after stressing in a weathering tester was furthermore determined. For this, a further film was applied to a glass plate in a layer thickness of 500 μm and this was stored/cured under standard climatic conditions for 2 weeks and then stressed for 72 hours (Q-Sun (72 h)) at a temperature of 65° C. in a model Q-Sun Xenon Xe-1 weathering tester having a Q-SUN Daylight-Q optical filter and a xenon lamp having a light intensity of 0.51 W/m$^2$ at 340 nm. The color difference ΔE of the thus stressed film versus the corresponding unstressed film was then determined using an NH310 colorimeter from Shenzen 3NH Technology Co. LTD equipped with silicon photoelectric diode detector, light source A, color space measurement interface CIE L*a*b*C*H*. ΔE values up to 5 represent slight yellowing.

The results are reported in table 1.

The examples labeled "(Ref.)" are comparative examples.

TABLE 1

Composition and properties of examples 1 to 6.

| | | Example | | | | |
|---|---|---|---|---|---|---|
| | 1 (Ref.) | 2 | 3 | 4 (Ref.) | 5 (Ref.) | 6 |
| Resin comp.: | | | | | | |
| Sikafloor ® -264N (A) | 450.0 | 450.0 | 450.0 | 450.0 | 450.0 | 450.0 |
| Curing agent comp.: | | | | | | |
| B-EDA | 42.6 | — | 39.7 | 33.3 | 35.1 | — |
| DB-EDA | — | — | 7.0 | 22.2 | — | — |
| B-EDA-mix | — | 46.7 | — | — | — | 38.5 |
| TEPA | 4.5 | 4.5 | 4.5 | 4.5 | 4.5 | 4.5 |
| Adduct-1 | — | — | — | — | 13.5 | 13.5 |
| Benzyl alcohol | 10.0 | 10.0 | 10.0 | 10.0 | 10.0 | 10.0 |
| Ca nitrate solution | 2.0 | 2.0 | 2.0 | 2.0 | 2.0 | 2.0 |
| Ancamine ® K54 | 2.0 | 2.0 | 2.0 | 2.0 | 2.0 | 2.0 |
| Weight ratio [1] | 100/0 | 85/15 | 85/15 | 60/40 | 100/0 | 85/15 |
| Viscosity (10') [Pa · s] | 1.9 | 1.8 | 1.8 | 1.8 | 2.5 | 2.3 |
| Shore D (1 d SCC) | 76 | 72 | 72 | 67 | 66 | 63 |
| (2 d SCC) | 80 | 76 | 76 | 71 | 71 | 73 |
| Shore D (1 d 8°/80%) | 42 | 43 | 49 | 17 | 38 | 35 |
| (2 d 8°/80%) | 72 | 73 | 75 | 55 | 65 | 64 |
| König (1 d SCC) | 63 | 60 | 62 | 43 | 52 | 45 |
| hardness [s] (2 d SCC) | 84 | 79 | 85 | 72 | 87 | 74 |
| (4 d SCC) | 102 | 92 | 99 | 88 | 104 | 92 |

TABLE 1-continued

Composition and properties of examples 1 to 6.

| | | 1 (Ref.) | 2 | 3 | 4 (Ref.) | 5 (Ref.) | 6 |
|---|---|---|---|---|---|---|---|
| | (7 d SCC) | 112 | 105 | 115 | 98 | 126 | 116 |
| | (14 d SCC) | 119 | 115 | 116 | 101 | 150 | 133 |
| Appearance (SCC) | | nice | nice | nice | nice | nice | nice |
| Q-Sun (72 h) ΔE | | 3.7 | 4.3 | 4.9 | 3.4 | 3.1 | 3.4 |
| König h. | (7 d 8°/80%) | 18 | 17 | 18 | 12 | 20 | 18 |
| [s] | (+2 d SCC) | 37 | 33 | 49 | 39 | 55 | 45 |
| | (+7 d SCC) | 59 | 55 | 60 | 48 | 70 | 64 |
| | (+14 d SCC) | 80 | 74 | 73 | 59 | 98 | 95 |
| Appearance | | | | | | | |
| | (8°/80%) | matt | nice | nice | nice | matt | nice |
| Blushing | | 1 | 0 | 0 | 0 | 1 | 0 |
| Ring | | slight | none | none | severe | average | none |

[1] weight ratio between N-benzylethane-1,2-diamine and N,N'-dibenzylethane-1,2-diamine

The invention claimed is:

1. A curing agent for epoxy resins comprising N-benzylethane-1,2-diamine and N,N'-dibenzylethane-1,2-diamine in a weight ratio in the range from 70/30 to 90/10, wherein the curing agent comprises a reaction mixture obtained from the reductive alkylation of ethane-1,2-diamine with benzaldehyde and hydrogen.

2. The curing agent as claimed in claim 1, wherein the curing agent comprises at least one further amine.

3. The curing agent as claimed in claim 2, wherein the further amine is selected from the group consisting of 2,2(4),4-trimethylhexane-1,6-diamine, 1,2-, 1,3- or 1,4-diaminocyclohexane, 1,3-bis(aminomethyl)cyclohexane, 1,4-bis(aminomethyl)cyclohexane, bis(4-aminocyclohexyl)methane, 1-amino-3-aminomethyl-3,5,5-trimethylcyclohexane, 2(4)-methyl-1,3-diaminocyclohexane, 1,3-bis(aminomethyl)benzene, polyoxypropylenediamines having an average molecular weight $M_n$ in the range from 200 to 500 g/mol, 3-(3-(dimethylamino)-propylamino)propylamine, bis(6-aminohexyl)amine, diethylenetriamine, triethylenetetramine, tetraethylenepentamine, pentaethylenehexamine, dipropylenetriamine, N-(2-aminoethyl)propane-1,3-diamine, N,N'-bis(3-aminopropyl)ethylenediamine, adducts of these or further polyamines with mono- or diepoxides and Mannich bases.

4. The curing agent as claimed in claim 2, wherein the further amine is 1-amino-3-aminomethyl-3,5,5-trimethylcyclohexane.

5. The curing agent as claimed in claim 2, wherein the further amine is 1,3-bis(aminomethyl)benzene.

6. The curing agent as claimed in claim 2, wherein the further amine is triethylenetetramine, tetraethylenepentamine, pentaethylenehexamine or N,N'-bis(3-aminopropyl)ethylenediamine.

7. The curing agent as claimed in claim 2, wherein the further amine is 3-(3-(dimethylamino)propylamino)propylamine.

8. An epoxy resin composition comprising
a resin component comprising at least one epoxy resin and
a curing agent component comprising the curing agent as claimed in claim 1.

9. The epoxy resin composition as claimed in claim 8, wherein the epoxy resin composition comprises at least one further constituent selected from the group consisting of thinners, accelerators and fillers.

10. A method comprising using the epoxy resin composition as claimed in claim 8 as coating, primer, adhesive, sealant, encapsulating compound, casting resin or as matrix for fiber composite materials.

11. An article obtained from the method as claimed in claim 10.

12. A method of coating, comprising the steps of
(i) mixing the components of the epoxy resin composition as claimed in claim 8,
(ii) applying the mixed composition to a substrate within the pot life,
followed by the curing of the mixed composition.

13. A method of bonding, comprising the steps of
(i) mixing the components of the epoxy resin composition as claimed in claim 8,
(ii) applying the mixed composition within the pot life, either to at least one of the substrates to be bonded and joining the substrates to form a bond within the open time,
or in a cavity or gap between two or more substrates and optionally inserting an anchor into the cavity or gap within the open time,
followed by the curing of the mixed composition.

14. The curing agent as claimed in claim 1, wherein the curing agent contains less than 2% by weight of N,N-dibenzylethane-1,2-diamine.

15. A curing agent for epoxy resins comprising N-benzylethane-1,2-diamine and N,N'-dibenzylethane-1,2-diamine in a weight ratio in the range from 80/20 to 90/10.

16. The curing agent as claimed in claim 15, wherein the curing agent comprises at least one further amine.

17. The curing agent as claimed in claim 16, wherein the further amine is selected from the group consisting of 2,2(4),4-trimethylhexane-1,6-diamine, 1,2-, 1,3- or 1,4-diaminocyclohexane, 1,3-bis(aminomethyl)cyclohexane, 1,4-bis(aminomethyl)cyclohexane, bis(4-aminocyclohexyl)methane, 1-amino-3-aminomethyl-3,5,5-trimethylcyclohexane, 2(4)-methyl-1,3-diaminocyclohexane, 1,3-bis(aminomethyl)benzene, polyoxypropylenediamines having an average molecular weight $M_n$ in the range from 200 to 500 g/mol, 3-(3-(dimethylamino)-propylamino)propylamine, bis(6-aminohexyl)amine, diethylenetriamine, triethylenetetramine, tetraethylenepentamine, pentaethylenehexamine, dipropylenetriamine, N-(2-aminoethyl)propane-1,3-diamine, N,N'-bis(3-aminopropyl)ethylenediamine, adducts of these or further polyamines with mono- or diepoxides and Mannich bases.

18. An epoxy resin composition comprising
a resin component comprising at least one epoxy resin and
a curing agent component comprising the curing agent as claimed in claim 15.

19. The epoxy resin composition as claimed in claim 18, wherein the epoxy resin composition comprises at least one further constituent selected from the group consisting of thinners, accelerators and fillers.

20. The curing agent as claimed in claim 15, wherein the curing agent contains less than 2% by weight of N,N-dibenzylethane-1,2-diamine.

* * * * *